United States Patent [19]

Hara et al.

[11] Patent Number: 4,614,430
[45] Date of Patent: Sep. 30, 1986

[54] METHOD OF DETECTING PATTERN DEFECT AND ITS APPARATAUS

[75] Inventors: Yasuhiko Hara; Yoshimasa Ohshima; Satoru Fushimi; Hiroshi Makihira, all of Yokohama, Japan

[73] Assignee: Hitachi Ltd., Tokyo, Japan

[21] Appl. No.: 604,998

[22] Filed: Apr. 27, 1984

[30] Foreign Application Priority Data

Apr. 28, 1983 [JP] Japan .................................. 58-73727
Sep. 9, 1983 [JP] Japan ................................ 58-165075

[51] Int. Cl.$^4$ ............................................. H06N 7/18
[52] U.S. Cl. ........................................ 356/394; 382/8
[58] Field of Search .................. 356/394; 382/8, 34, 382/45

[56] References Cited

U.S. PATENT DOCUMENTS 4,421,410 12/1983 Karasaki .............................. 356/394
4,508,453 4/1985 Hara et al. ......................... 356/394

FOREIGN PATENT DOCUMENTS 196377 12/1982 Japan .

*Primary Examiner*—R. A. Rosenberger
*Attorney, Agent, or Firm*—Antonelli, Terry & Wands

[57] ABSTRACT

A pattern defect is detected in accordance with the difference between a pair of patterns. The patterns are scanned and imaged to obtain first and second binary signals. A positioning error between the patterns is two-dimensionally detected during the scanning with respective first and second binary signals delayed by a prescribed amount so that each of the picture elements in a prescribed area of a two-dimensional image, delayed and cut out two-dimensionally, corresponding to one pattern, is compared with a specified picture element in a predetermined area of an image delayed and cut out two-dimensionally corresponding to another pattern. The result of the comparison is statistically summed to derive a positioning error by detecting the position shown as an extreme value from the summed values. The positioning error is corrected by two-dimensionally shifting at least one of the delayed binary signals. The corrected binary signals are then two-dimensionally compared with each other.

7 Claims, 44 Drawing Figures

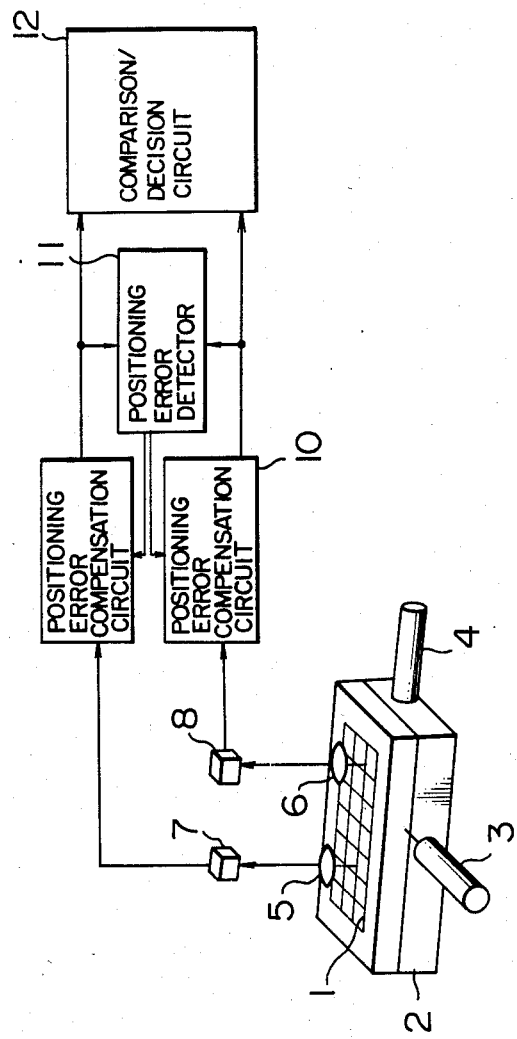

METHOD OF DETECTING PATTERN DEFECT AND ITS APPARATAUS

The present invention relates to a method of and an apparatus for automatically and accurately detecting a defect in a circuit pattern formed on an LSI wafer, photomask, or printed wiring board, and more particularly to a method of and an apparatus for automatically detecting defects in a multi-layer aluminum wiring pattern formed on the surface of an LSI wafer, such as the short circuit or disconnection of wiring and the unevenness of wiring pattern.

In order that an LSI and others are made small in size and moreover can perform various functions, the packing density thereof has been increased. However, in order to assure the reliability thereof, it is necessary to previously inspect a circuit pattern formed thereon, and to detect and remove defects in the circuit pattern rapidly. Accordingly, a mask inspection apparatus capable of comparing a pair of patterns has been developed and put to practical use, to be used in place of a visual inspection device using a microscope. In the mask inspection apparatus, a pattern to be inspected is compared with a reference pattern, to judge whether a pattern defect is present in the to-be-inspected pattern or not. In the case where the to-be-inspected pattern is compared with the reference pattern, the positional relation between these patterns is very important. If a positioning error exists between the patterns, a pattern defect smaller than the positioning error will not be detected. In the conventional mask inspection apparatus, the positioning of patterns has been made with desired accuracy by increasing the mechanical accuracy of a stage for scanning patterns and the mechanical accuracy of an optical system for detecting the patterns. However, the positioning accuracy with respect to the positional relation between patterns cannot be made higher than the present one. In more detail, though the required positioning accuracy increases as the width of patterns is smaller, each pattern has its own positioning error which is introduced in forming the pattern. Accordingly, it is not possible to arrange two fine patterns with desired accuracy only by increasing the mechanical positioning accuracy, and therefore small defects cannot be detected.

As mentioned above, a limit is placed on the mechanical positioning. In order to solve this problem, it has been proposed to electrically measure a positioning error between patterns and to correct the positioning error. Such a method is disclosed in, for example, a Japanese Patent Application Specification (Laid-open No. 196377/1982). Though this method offers a new problem, the outline of the method will be explained below.

As shown in FIG. 1, a sample 1 such as a mask is placed on a stage 2 which is moved in X- and Y-directions by driving motors 3 and 4. Optical images of similar pattern portions on a pair of chips which are included in the sample 1 and have the same shape, are formed of object lenses 5 and 6, and are converted by pattern detectors 7 and 8 (for example, TV cameras or solid image pickup devices) into electrical signals. A pair of binary signals substantially equal to each other are delivered from the pattern detectors 7 and 8, and are compared with each other by a comparison/decision circuit 12, to compare patterns on the chips. When the binary signals are different from each other, it is judged by the circuit 12 that a defect is present in one of the patterns. As shown in FIG. 1, prior to the comparison of the patterns, a positioning error between the patterns is detected by a positioning error detector 11. In the case where at least one of the pattern detectors 7 and 8 is deviated from a desired position, there is a possibly of judging a normal pattern to be a defective pattern. Accordingly, the positioning error is electrically corrected by positioning error compensation circuits 9 and 10, on the basis of positioning error correction data from the positioning error detector 11. The binary signals thus corrected are compared with each other by the comparison/decision circuit 12, and thus the patterns are compared with each other.

In the positioning error detector 11, the positioning error in the X-direction and the positioning error in the Y-direction are detected. FIGS. 2A and 2B are views for explaining the principle on which the positioning error in the X-direction is detected. According to this principle, a binary pattern on the left and a binary pattern on the right are cut off by shift registers so as to form local patterns, and are moved in an IC memory two-dimentionally (namely, in the direction from left to right and the direction from top to bottom), in synchronism with the scanning operation of the pattern detectors 7 and 8. The view on the left-hand side of FIG. 2A shows an example of the pattern arranged on the left-hand side of the IC memory, and the view on the left-hand side of FIG. 2B shows an example of the pattern arranged on the right-hand side of the IC memory. In the IC memory, these patterns are converted into edge patterns, as indicated by the views on the right-hand side of FIGS. 2A and 2B, and then the positioning error is measured. That is, the positioning error in the X-direction is measured after each edge pattern has been projected onto the Y-axis and expressed in terms of binary codes. In the above-mentioned example, the pattern arranged on the left-hand side of the IC memory is coded in the form of "000000110", and the pattern arranged on the right-hand side is coded in the form of "011000000". Thus, it is known that the positioning error in the X-direction is +5 bits. The positioning error in the Y-direction can be detected in a similar manner. The above-mentioned detection of the positioning error is carried out a multiplicity of times. The positioning error data thus obtained is statistically processed, and thus the most probable positioning error is detected.

Then, the positioning error correction is made for one of the binary signals, on the basis of the most probable positioning error. FIG. 3 shows the positioning error correction principle. As shown in FIG. 3, a two-dimensional local pattern memory is formed of n shift registers each having m bits, and a desired output is taken out of a bit position corresponding to detected positioning errors X and Y. It is equivalent to advance one of the binary signals that the other binary signal is delayed. Accordingly, a correct positional relation between the left and right patterns can be attained electrically, by carrying out the positioning error correction for one of the binary signals. FIG. 4 shows an actual circuit configuration for carrying out the positioning error correction. Referring to FIG. 4, the output at a desired bit position in the Y-direction is selected from the outputs of a two-dimensional pattern cut-off circuit 14 by a multiplexer 15, and is shifted in a shift register 16 for series to parallel conversion. Then, the output at a desired bit position in the X-direction is selected from the parallel outputs of the shift register 16 by a multiplexer 17.

According to the above-mentioned method, a pattern arranged in the X- and Y-directions can be readily processed. However, for a pattern arranged in directions other than the X- and Y-directions such as a 45° pattern, it is impossible to detect and correct the positioning error. Further, since the positioning error detection and the positioning error correction are time-sequentially switched, the patterns may be extinguished or deformed before or after the positioning error correction. Thus, there is a possibility of information on a fine defect being lost. That is, it is impossible to make an accurate inspection of a pattern. Accordingly, it is necessary to make the positioning error correction at a position where no pattern exists. Further, according to the above method, a time the positioning error is measured, is different from a time a pattern defect is detected. Accordingly, in the case where a continuous pattern speads over a wide area, a pattern portion where the positioning error is measured, is spaced apart from a pattern portion where a pattern defect is to be detected. Thus, it is impossible to accurately correct the positioning error.

In some samples which are high in pattern density, each chip has an area where no pattern exists. For such a case, it has been proposed in a Japanese Patent Application Specification (Laid-open No. 34402/1982) that positioning error correction is made when the pattern detector passes across a dicing line including no pattern (that is, the boundary between adjacent chips). According to this method, however, a chip where the positioning error is measured, is different from a to-be-inspected chip, and moreover the positioning accuracy of the stage and the arrangement accuracy of chips may vary in a period when the pattern detector passes one chip. Accordingly, the precise positioning of two patterns cannot be made, and it is impossible to detect a pattern defect with high accuracy.

A further method of electrically correcting the positioning error is described in an article entitled "AUTOMATIC INSPECTION OF MASK DEFECTS" (SPIE, Vol. 100, Semiconductor Microlithography, 11, pages 26 to 32, 1977).

It is accordingly an object of the present invention to provide a method of and an apparatus for detecting a pattern defect, in which a positioning error between two patterns to be compared can be accurately detected even when each pattern includes a partial pattern formed in directions other than the X- and Y-directions, and thus a defect in one of the patterns can be detected with high accuracy.

In order to attain the above object, according to the present invention, there is provided a method of detecting a pattern defect, in which each time two binary signals corresponding to a pair of patterns are delayed by a predetermined amount, a positioning error existing between the patterns is detected in the delay period in such a manner that each of picture elements included in a predetermined area of a two-dimensional image corresponding to one of the patterns which has been two-dimensionally delayed, is compared with a specified picture element included in an image corresponding to the other pattern which has been similarly delayed, the result of comparison is summed at each of the former picture elements to detect the positioning error, the positioning error correction is made for the binary signals on the basis of the detected positioning error, and then the binary signals thus corrected are compared with each other to detect a defect in one of the patterns. In other words, according to this method, the same portion of a binary signal is used both for detecting the positioning error and for detecting the pattern defect.

Further, according to the present invention, there is provided an apparatus for detecting a pattern defect, which comprises means for delaying two binary signals corresponding to a pair of patterns by a predetermined amount, and means for detecting a positioning error between the patterns, in a period when the binary signals are delayed by the predetermined amount, by comparing each of picture elements included in a predetermined area of a two-dimensional image corresponding to one of the patterns which has been two-dimentionally delayed, with a specified picture element included in an image corresponding to the other pattern which has been delayed, and by summing the result of comparison at each of the former picture elements.

In the case where a pair of wiring patterns formed on a wafer are compared with each other to detect a defect in one of the wiring patterns, it is necessary to clearly show the wiring patterns. According to the present invention, there is further provided a method of increasing the quantity of light reflected from a planar portion of a specified wiring pattern by illuminating the wiring pattern with dark field illumination light to such an extent as to be able to detect the reflected light from the surface of the wiring pattern, and further illuminating the wiring pattern with vertical illumination light. When this method is carried out, it is desirable to make the quantity of dark field illumination light larger than the quantity of vertical illumination light and to make high the light detection level of a pattern detector, since the picture quality of the image of the wiring pattern is improved.

In order to readily carry out the above-mentioned method and to exhibit the remarkable effect of the method, according to the present invention, there is provided an illumination device in which a lamp for vertical illumination and a lamp for dark field illumination are severally provided, means for adjusting the quantity of light from the vertical illumination lamp is provided to adjust a ratio of the quantity of light from the vertical illumination lamp to the quantity of light from the dark field illumination lamp, a first parabolic mirror is disposed so as to reflect the light from the dark field illumination lamp in directions parallel to the optical axis of an object lens, and a second parabolic mirror is provided in the vicinity of an end portion of the object lens to reflect the dark field illumination light made parallel to the optical axis of the object lens, in directions toward a portion to be illuminated.

The present invention will be apparent from the following detailed description taken in conjunction with the accompanying drawings, in which:

FIG. 1 is a schematic view showing the outline of a conventional pattern defect detecting apparatus;

FIGS. 2A, 2B, 3, and 4 are views for explaining the positioning error correction principle used in the conventional apparatus shown in FIG. 1;

FIG. 5 is a block diagram showing the circuit configuration of an embodiment of a pattern defect detecting apparatus according to the present invention;

FIGS. 6, 7, and 8 are circuit diagrams showing respective examples of the matching detection circuit, correction circuit, and comparison circuit shown in FIG. 5;

Figure 13A:
Figure 13C:
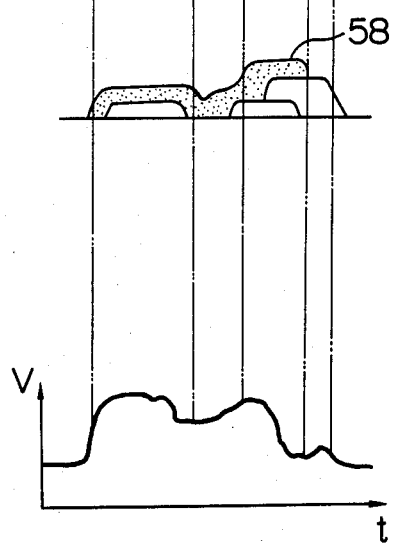
Figure 14A:
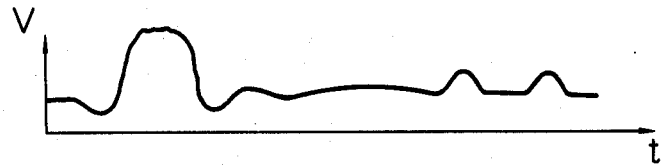
Figure 14B:
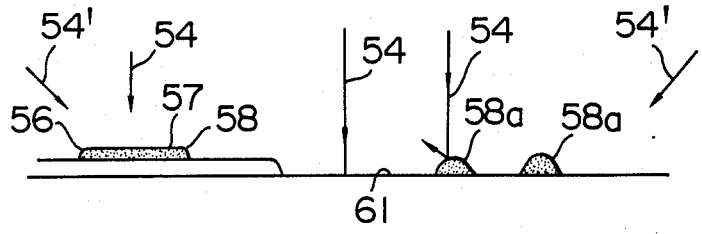
Figure 15A:
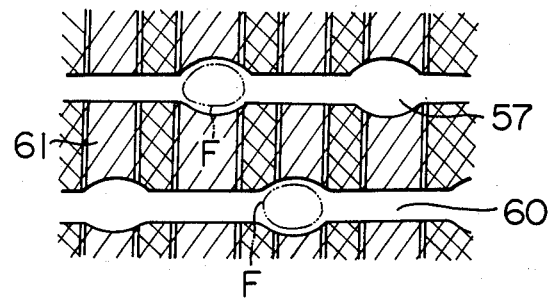
Figure 15B:
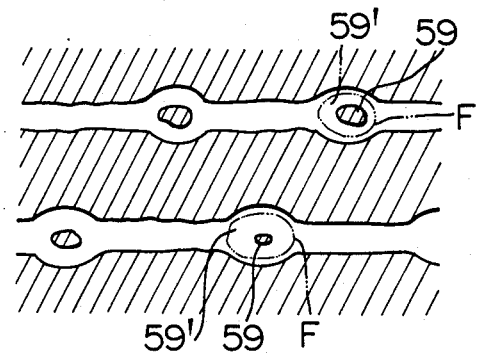
Figure 15C:
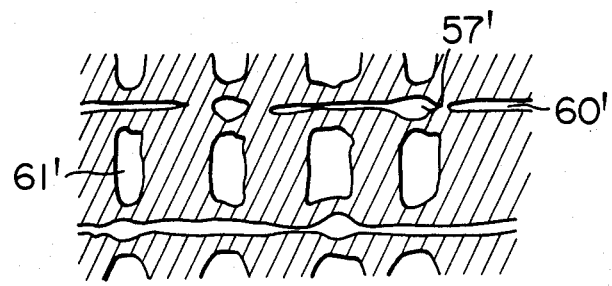
Figure 15D:
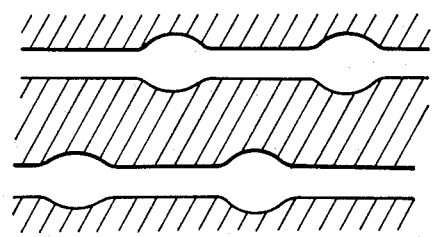
Figure 16A:
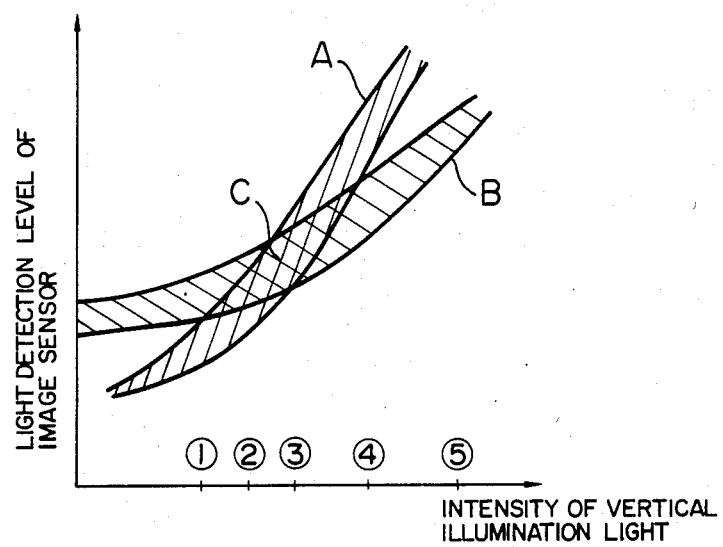
Figure 16B:
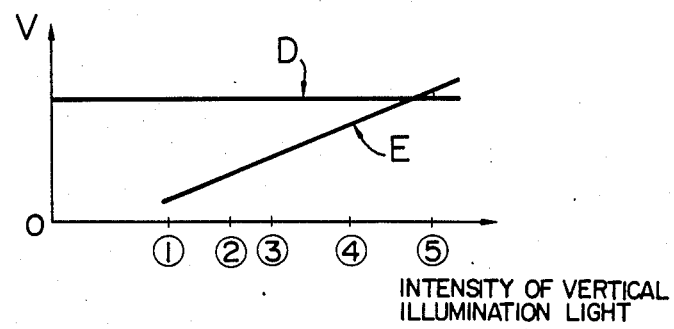

FIGS. 13A to 13D show relations between an aluminum wiring pattern formed on a wafer and detection signals, FIG. 13A is a graph showing a detection signal based upon vertical illumination, FIG. 13B is a graph showing a detection signal based upon dark field illumination, FIG. 13C is a cross-sectional view showing the aluminum wiring pattern on the wafer, and FIG. 13D is a graph showing a detection signal based upon both vertical illumination and dark field illumination;

FIG. 14A and 14B show a relation between an aluminum wiring pattern formed on a wafer and a detection signal, FIG. 14A is a graph showing the detection signal, and FIG. 14B is a sectional view showing a surface portion of the wafer;

FIGS. 15A to 15D show an aluminum wiring pattern formed on a wafer and detected images of the wiring pattern, FIG. 15A is a plan view showing the wiring pattern on the wafer, FIG. 15B shows an image which is detected when the wiring pattern is subjected to strong, dark field illumination, FIG. 15C shows an image which is detected when the wiring pattern is subjected to strong, vertical illumination, and FIG. 15D shows a desirable, detected image;

FIG. 16A and 16B are graphs for explaining illumination conditions under which favorable images of the wiring pattern can be detected.

Figure 2A:
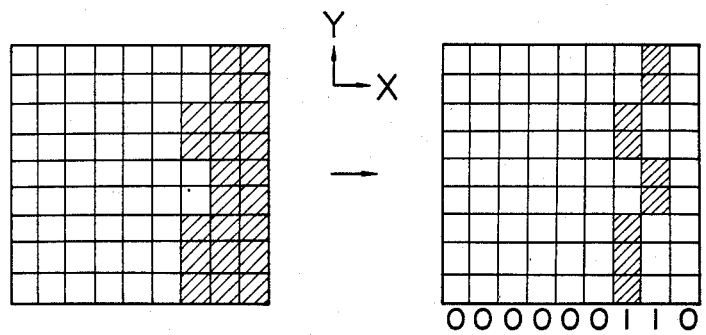
Figure 2B:
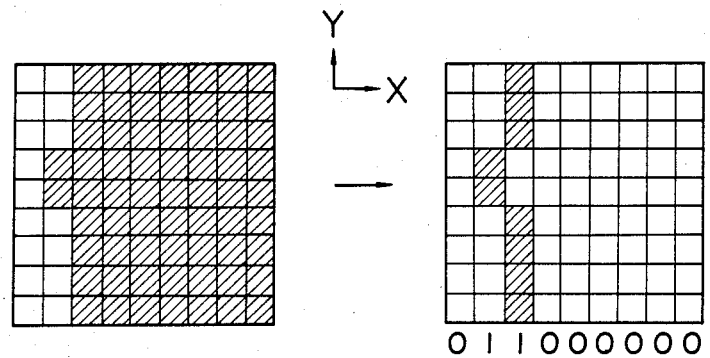
Figure 3:
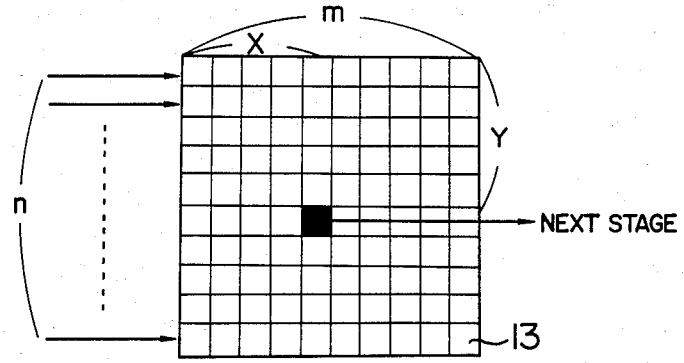
Figure 4:
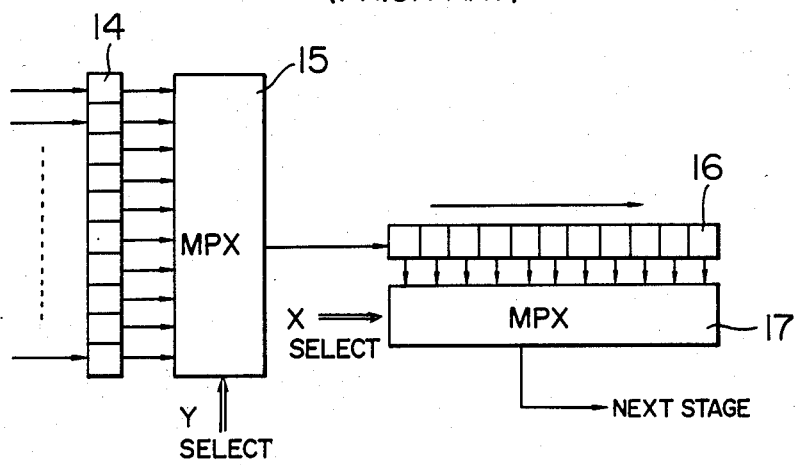
Figure 5:
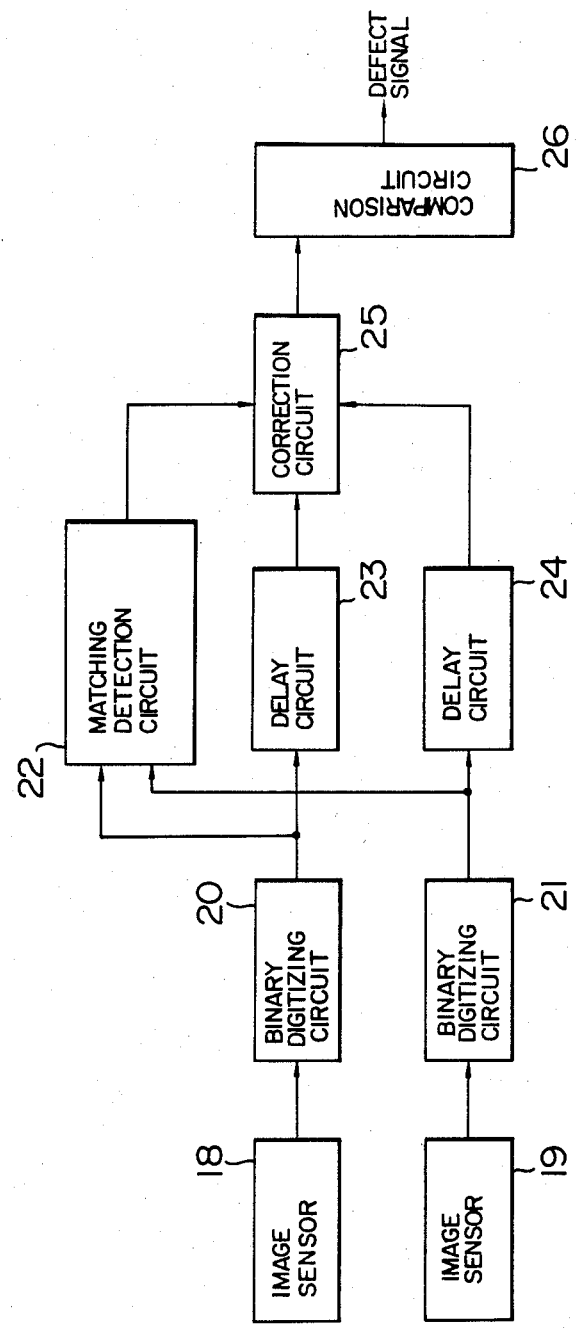
Figure 17:
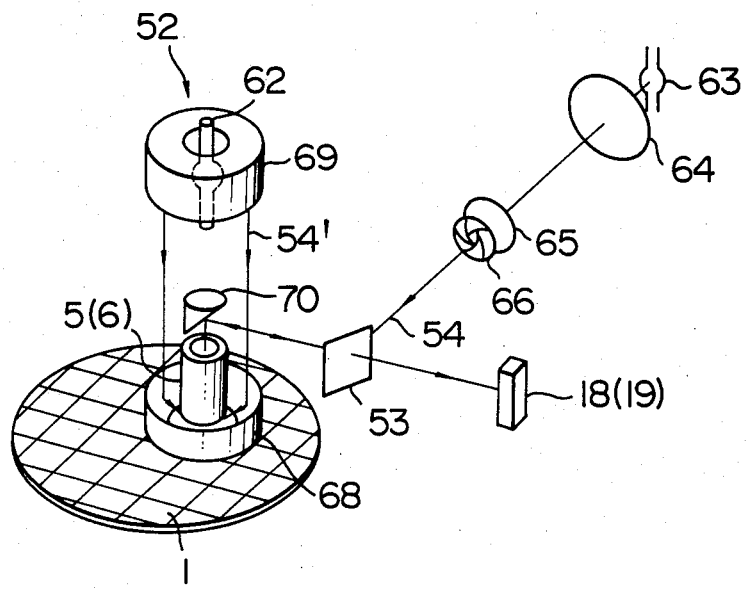
Figure 18:
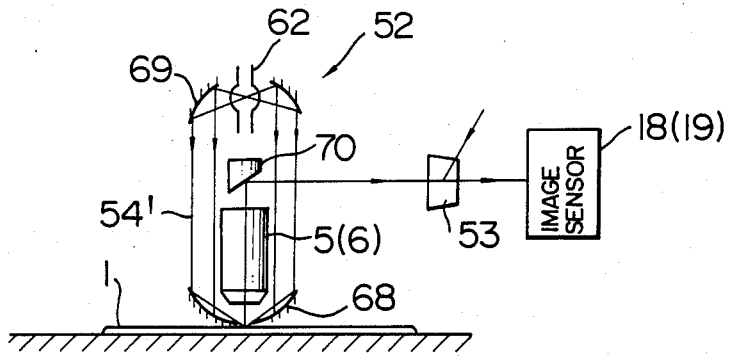
Figure 19:
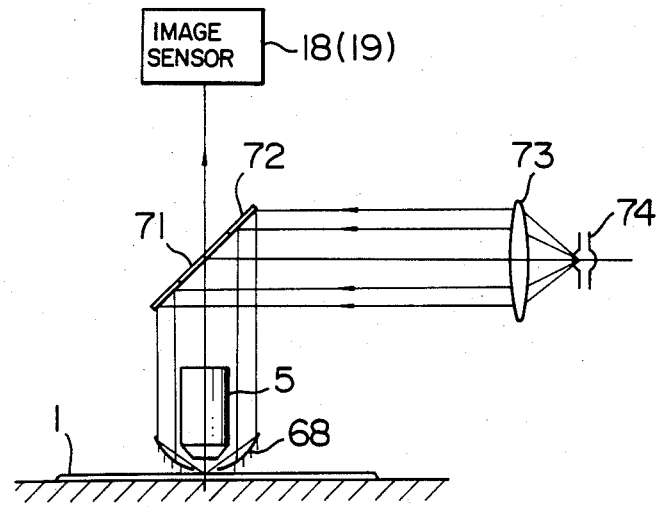
Figure 20:
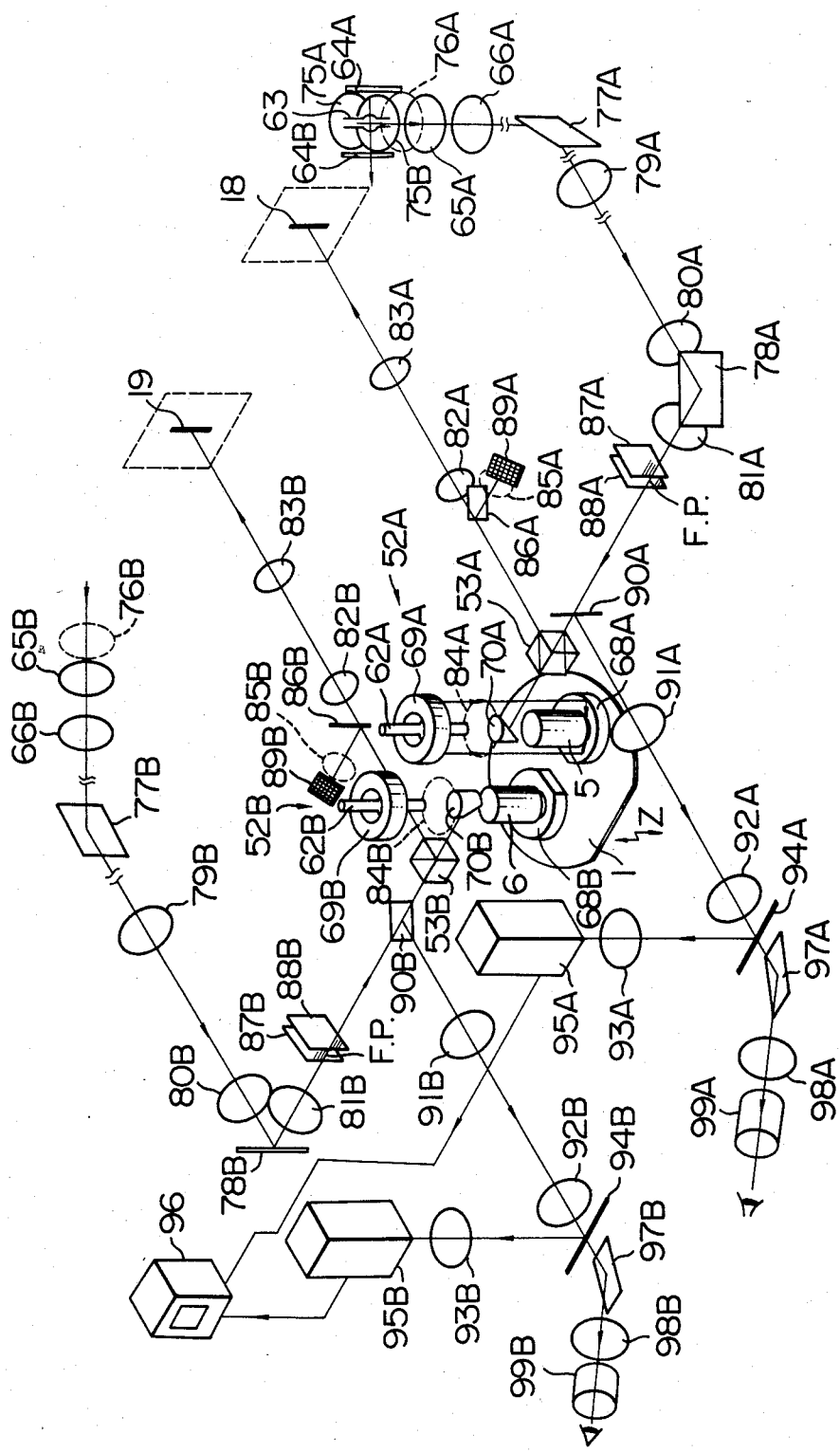

FIG. 17 is an arrangement view showing an example of a wafer illuminating device according to the present invention;

FIG. 18 is a schematic view showing the dark field illumination system shown in FIG. 17;

FIG. 19 is a schematic view showing a conventional illumination system for both dark field illumination and vertical illumination; and FIG. 20 is an arrangement view showing an example of an optical system used in the embodiment shown in FIG. 5.

Now, the pattern defect detection according to the present invention will be explained below, with reference to FIGS. 5 to 11.

First, explanation will be made on the construction and operation of an embodiment of a pattern defect detecting apparatus according to the present invention, with reference to FIG. 5. Linear image sensors 18 and 19 (each formed of a charge coupled device or others) act as pattern detectors, and one-dimensionally detect patterns on the basis of self-scanning. When a sample fixed to a stage is subjected to sub-scanning in a direction perpendicular to the self-scanning direction, two patterns formed on the sample and having the same shape can be two-dimensionally detected by the linear image sensors 18 and 19. An imaging apparatus such as a television camera may be used in place of the linear image sensor. In the case where the television camera is used, if a point to be detected can be imaged a plurality of times, delay circuits 23 and 24 shown in FIG. 5 can be omitted.

The outputs of the linear image sensors 18 and 19 are converted by binary digitizing circuits 20 and 21 into binary picture element signals, which are applied to a mathing detection circuit 22 and delay circuits 23 and 24. Each of the delay circuits 23 and 24 may be formed of a D-RAM, and operated in the same manner as a shift register. Although details of the matching detection circuit 22 will be explained later, the circuit 22 detects a positioning error between two patterns, on the basis of the binary picture element signals, in a period when the binary picture element signals are delayed by the delay circuits 23 and 24. The amount of delay at each delay circuit is determined by M and N to be $M \times N$ bits where M (for example, 1,024) is a number of picture elements included in each linear image sensor 18, 19 and N (for example, 256) is a number of scanning operations of each linear image sensor 18, 19 which are required for detecting the positioning error. Accordingly, each of the delay circuits 23 and 24 can be formed, for example, by connecting N shift registers each having M bits, in cascade. Thus, the positioning errors in the X- and Y-directions are detected by and delivered from the matching detection circuit 22 each time the binary picture element signals are delayed by $M \times N$ ($= 1,024 \times 256$) bits, that is, each time N scanning operations are performed. The delayed binary picture element signal from the delay circuit 23 is shifted by the correction circuit 25 in accordance with the positioning errors from the matching detection circuit 22. Accordingly, a binary picture element signal having no positioning error for the binary picture element signal from the delay circuit 24 is delivered from the correction circuit 25. Thus, the patterns are compared with each other at a comparison circuit 26, using a pair of two-dimensional, binary picture element signals having no positioning error therebetween, and a defect in one of the patterns can be detected with high accuracy. The above-mentioned shifting in the correction circuit 25 is carried out in synchronism with a start pulse whenever the linear image sensors 18 and 19 have performed the scanning operation N times. Accordingly, the two-dimensional patterns memorized in two dimensional memory by binary picture element signals are not deviated from each other. Further, the same two-dimensional binary picture element signals are used for detecting the pattern defect and the positioning error. Accordingly, the pattern defect can be detected with high accuracy.

Next, the matching detection circuit, correction circuit, and comparison circuit shown in FIG. 5 will be explained below in detail.

Figure 6:
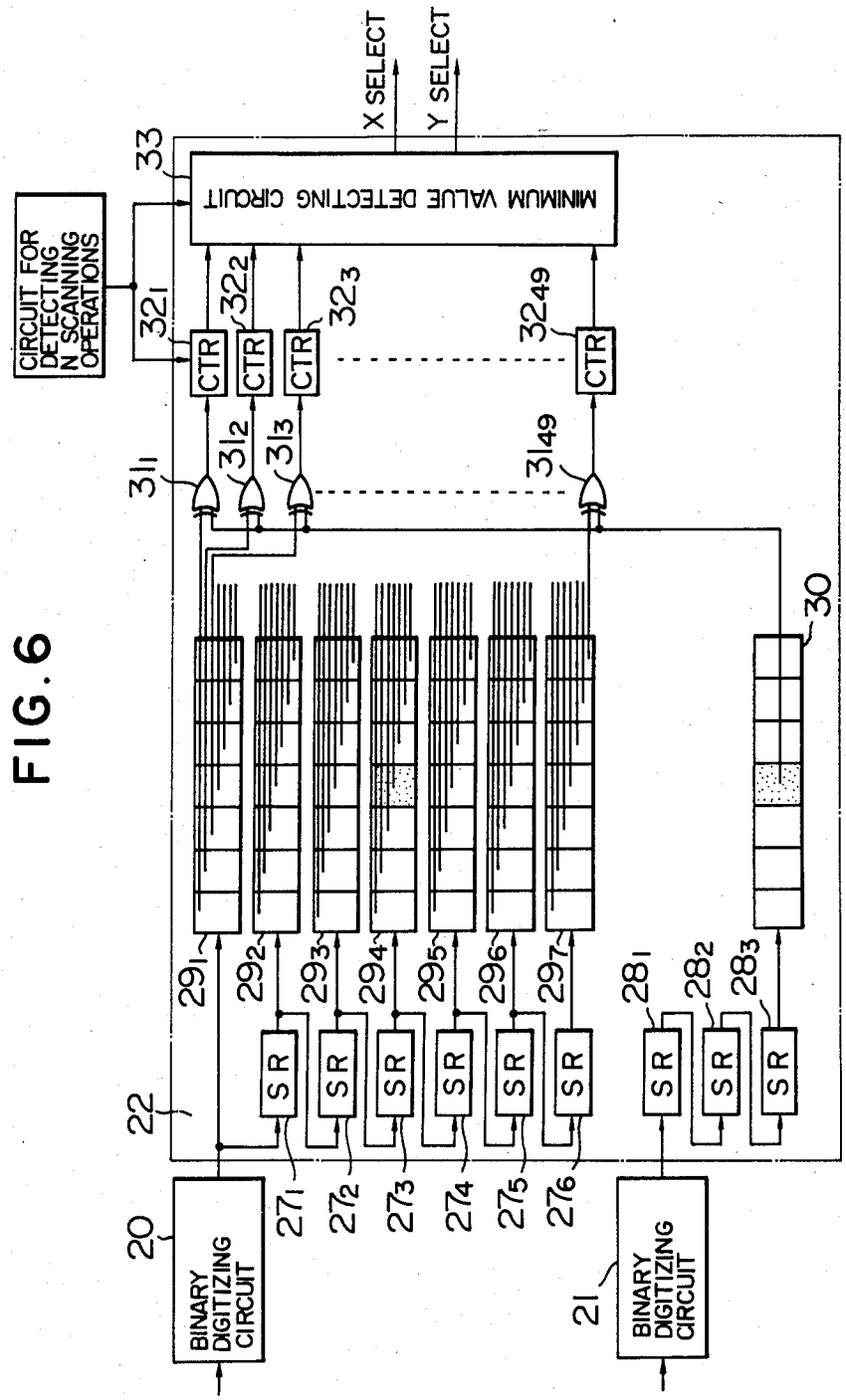

FIG. 6 shows the circuit configuration of an example of the matching detection circuit. Referring to FIG. 6, the binary picture element signal from the binary digitizing circuit 20 is cut out, in the form of a two-dimensional local pattern having $7 \times 7$ picture elements, by shift registers $27_1$ to $27_6$ and series-in parallel-out shift registers $29_1$ to $29_7$. Each of the shift registers $27_1$ to $27_6$ includes bits corresponding to one scanning operation of the linear image sensor, and the shift registers $29_1$ to $29_7$ make up a two-dimensional local memory. While, the binary picture element signal from the binary digitizing circuit 21 is cut out, in the form of a one-dimensional local pattern having $1 \times 7$ picture elements, by shift registers $28_1$ to $28_3$ and a series-in parallel-out shift register 30. This local pattern is cut out in synchronism with the data on the shift register $29_4$ which is disposed on the center line of the two-dimensional local memory. Each of the shift registers $28_1$ to $28_3$ includes bits corresponding to one scanning operation of the linear image sensor, and the shift register 30 serves as a one-dimensional local memory. Whenever one bit of binary picture element signal is delivered from each binary digitizing circuit, the exclusive logical sum of the output from the fourth bit position of the shift register 30 and the output from each bit position of the two-dimensional local memory is obtained by exclusive-OR gates $31_1$ to $31_{49}$. Thus, a picture element of the two-dimensional local memory which is different in output from the fourth bit position of the shift register 30, can be detected. Counters $32_1$ to $32_{49}$ are connected to the exclusive-OR gates $31_1$ to $32_{49}$, respectively. When a picture element of the two-dimensional local memory is different in output from the fourth bit position of the shift register 30, a corresponding counter is incremented by one. The counters $32_1$ to $32_{49}$ are reset whenever the linear image sensors have performed the scanning operation N times. Accordingly, the contents of each counter obtained immediately before the resetting of the counters indicate how many times each picture element of the two-dimensional local memory is different in output from the fourth bit position of the shift register 30 when M ×N picture elements of the pattern on the sample are scanned.

As is apparent from FIG. 6, the output at a picture element of the two-dimensional local memory $29_1$ to $29_7$ deviates from the output at the fourth bit position of the shift register by an amount which does not exceed ±3 picture elements, in each of the X- and Y-directions. Accordingly, it is evident that the output at a picture element (of the two-dimensional local memory) corresponding to a counter showing a minimum value is coincident with the output at the fourth bit position of the shift register 30. Thus, a matching position is detected. That is, a positioning error which does not exceed ±3 picture elements in each of the X- and Y-directions, can be automatically determined. A minimum value detecting circuit 33 takes in the contents of each counter at a time immediately before the resetting of the counter, detects a counter showing a minimum value, and delivers the positioning errors in the X- and Y-directions. Although the circuit construction shown in FIG. 6 can detect a positioning error which does not exceed ±3 picture elements, in each of the X- and Y-directions, the matching detection circuit is not limited to such circuit construction.

Figure 7:
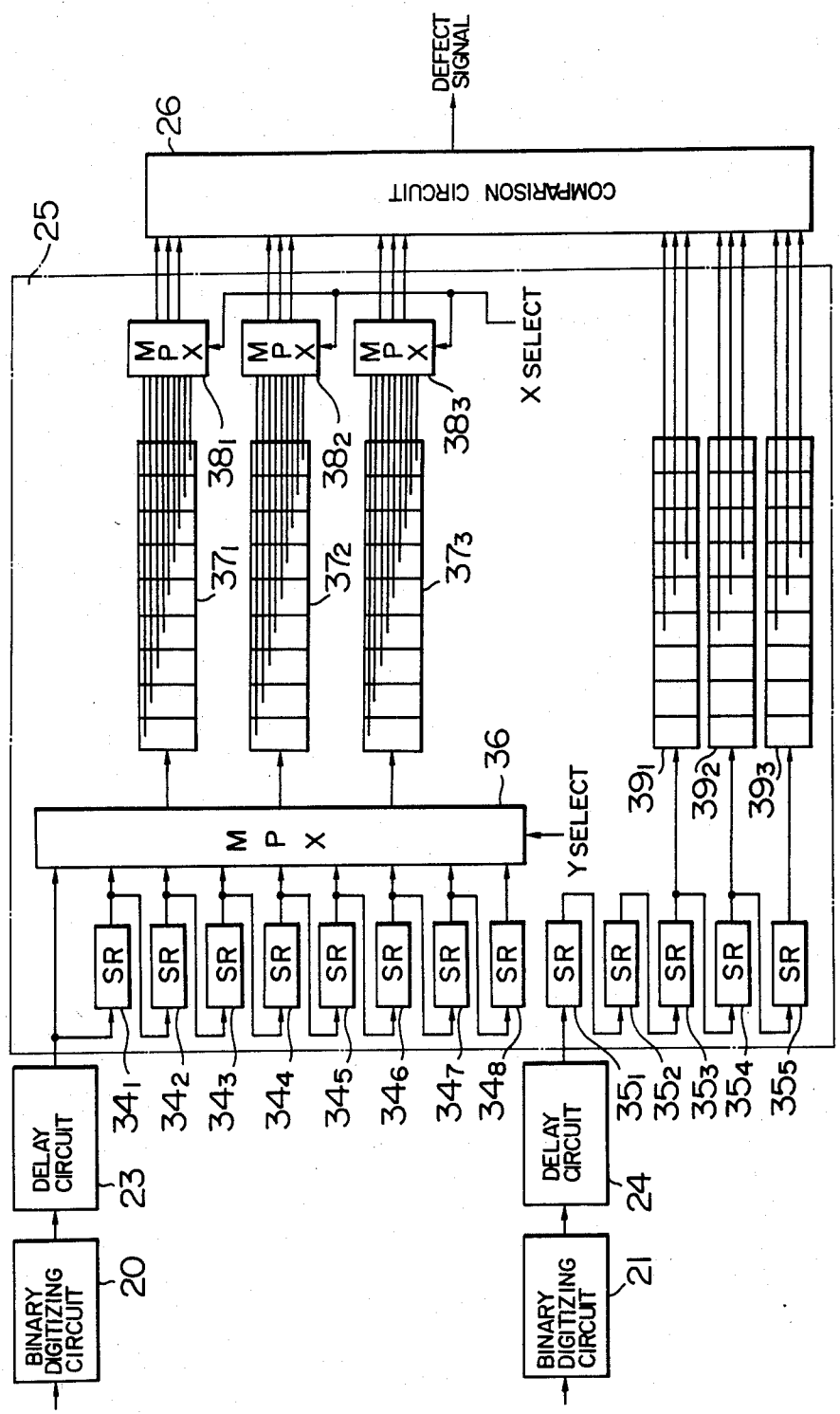

Next, the correction circuit will be explained below, with reference to FIG. 7. The binary signal from the binary digitizing circuit 20 is delayed by the delay circuit 23 by an amount corresponding to N scanning operations, and then applied to the correction circuit 25. A signal indicating the positioning error in the X-direction (hereinafter referred to as "X-select signal") and a signal indicating the positioning error in the Y-direction (hereinafter referred to as "Y-select signal") are applied from the minimum detection circuit 33 to the correction circuit 25. In the correction circuit 25, a binary signal corresponding to the output of the fourth bit position of the shift register 30 and binary signals which deviate from the above output by ± one picture element in the X- and Y-directions, are extracted by the X-select signal and Y-select signal.

Now, let us suppose that the scanning direction of the linear image sensors is the X-direction. Then, the shifted output at an optimum position in the Y-direction and the shifted outputs at positions deviated from the optimum position in the Y-direction by ±1 picture element are simultaneously selected, by a multiplexer 36, from the output of the delay circuit 23 and the outputs of the shift registers $34_1$ to $34_8$. Each of the shift registers $34_1$ to $34_8$ delays the input thereof by amount corresponding one scanning operation. The outputs thus selected are applied to the shift registers $37_1$ to $37_3$. From the outputs of the shift registers $37_1$ to $37_3$, the output at an optimum bit position in the X-direction and the outputs at bit positions deviating from the optimum bit position in the X-direction by ±1 picture element are selected by multiplexers $38_1$ to $38_3$. Thus, a binary signal corresponding to 3×3 picture elements which exist around an optimum bit position, is delivered from the multiplexers $38_1$ to $38_3$.

While, a binary signal which is to be compared, at the comparison circuit 26, with the above-mentioned binary signal corresponding to the 3×3 picture elements, is extracted from the binary signal which is outputted from the delay circuit 24. The binary signal from the delay circuit 24 are delayed by shift registers $35_1$ to $35_5$, and is applied to shift-registers $39_1$ to $39_3$ as shown in FIG. 7. Each of the shift registers $35_1$ to $35_5$ delays the input thereof by an amount corresponding to one scanning operation. The outputs at the fourth to sixth bit positions of each of the shift registers $39_1$ to $39_3$ are extracted to obtain a binary signal which is to be compared with the binary signal from the multiplexers $38_1$ to $38_3$. Thus, a pair of 9-bit binary signals are compared with each other at the comparison circuit 26.

Figure 8:
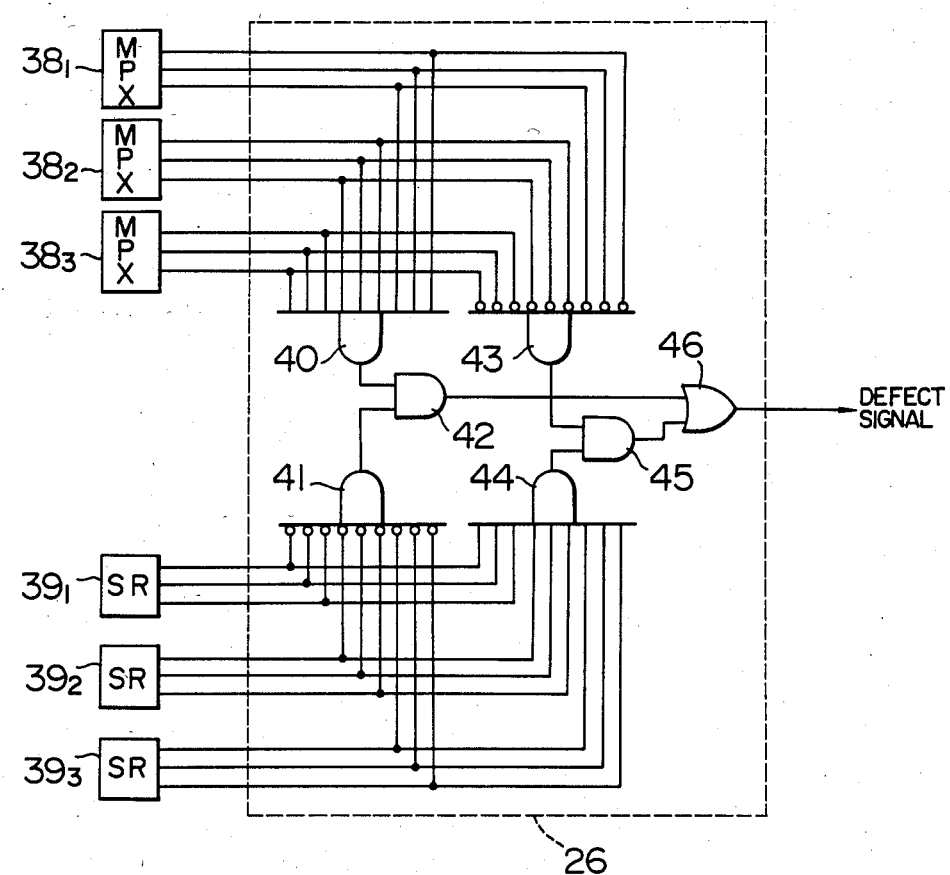

FIG. 8 is a circuit diagram showing an example of the comparison circuit 26. Referring to FIG. 8, it is judged by an AND gate 40 and an NOR gate 43 whether all bits of the 9-bit binary signal from the multiplexers $38_1$ to $38_3$ take the level of "1" or the level of "0". Similarly, it is judged by an AND gate 44 and an NOR gate 41 whether all bits of the 9-bit binary signal from the shift registers $39_1$ to $39_3$ take the level of "1" or the level of "0". In the case where all bits of the binary signal from the multiplexers $38_1$ to $38_3$ take the level of "1" and all bits of the binary signal from the shift registers $39_1$ to $39_3$ take the level of "0", the output of an AND gate 42 takes the level of "1". In the case where all bits of the binary signal from the multiplexers $38_1$ to $38_3$ take the level of "0" and all bits of the binary signal from the shift registers $39_1$ to $39_3$ take the level of "1", the output of an AND gate 45 takes the level of "1". In these cases, the output of an OR gate 46 takes the level of "1". That is, it is judged that a pattern defect is present.

Figure 9A:
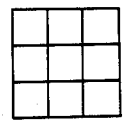
FIGS. 9A to 9F are views showing examples of axially symmetric picture element patterns.
Figure 9B:
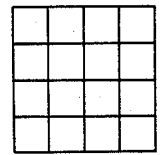
Figure 9C:
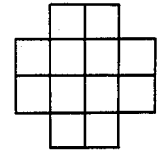
Figure 9D:
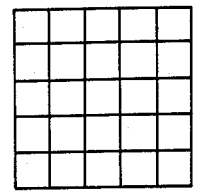
Figure 9E:
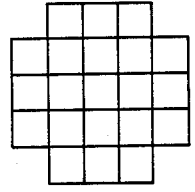
Figure 9F:
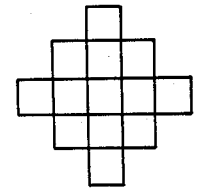
Figure 10A:
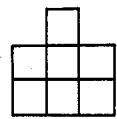
FIGS. 10A to 10H are views showing examples of axially asymmetric picture element patterns.
Figure 10B:
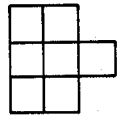
Figure 10C:
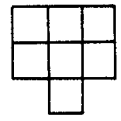
Figure 10D:
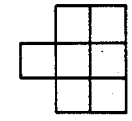
Figure 10E:
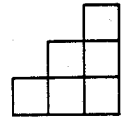
Figure 10F:
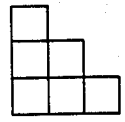
Figure 10G:
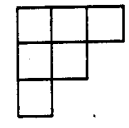
Figure 10H:
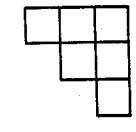

In the above-mentioned explanation, in order to detect a pattern defect, a pattern to be inspected has been compared with a reference pattern, using a 3×3 picture element pattern shown in FIG. 9A. However, axially symmetric patterns such as 4×4 picture element patterns shown in FIGS. 9B and 9C and 5×5 picture element patterns shown in FIGS. 9D to 9F may be used in place of the 3×3 picture element pattern, to change the defect detection sensitivity. The defect detection sensitivity decreases as the number of picture elements included in a picture element pattern is larger. In the case where one of the picture element patterns shown in FIGS. 9B to 9F is used, it is required to increase the number of shift registers such as the shift registers $34_1$ to $34_8$, the number of shift registers such as the shift register $35_1$ to $35_5$, the number of shift registers such as the shift registers $37_1$ to $37_3$, the number of shift registers such as the shift registers $39_1$ to $39_3$ and the number of bits included in each of shift registers such as the shift registers $37_1$ to $37_3$, and to increase the number of bits included in each of shift registers such as the shift registers $39_1$ to $39_3$, if necessary. Further, axially asymmetric patterns shown in FIGS. 10A to 10H may be used as a picture element pattern.

Figure 11A:
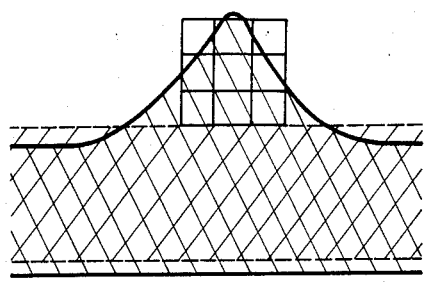
FIGS. 11A to 11D are views for explaining advantages of axially asymmetric picture element patterns.
Figure 11B:
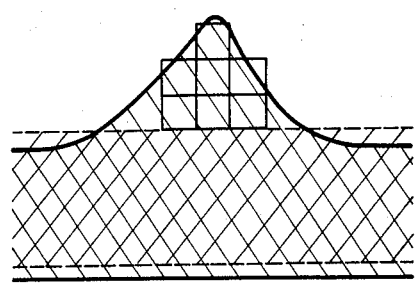
Figure 11C:
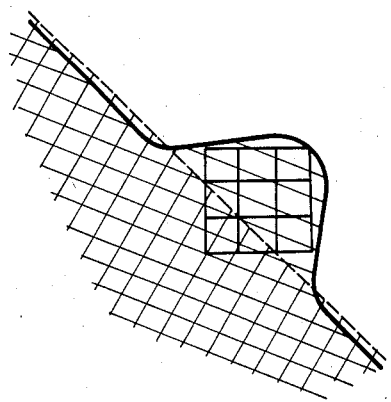
Figure 11D:
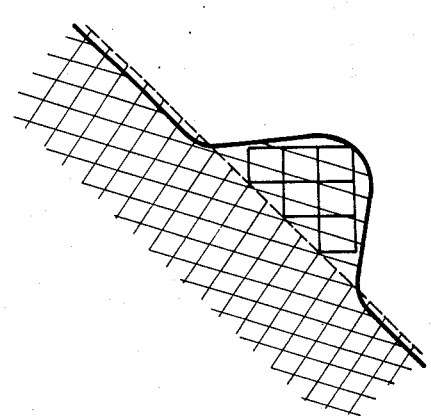

FIGS. 11A and 11B show the case where one of two patterns (indicated by different hatched areas) to be compared has a semicircular protrusion as a pattern defect. As is apparent from FIG. 11A, it is impossible to detect the defect by using the picture element pattern shown in FIG. 9A. However, as is known from FIG. 11B, the defect can be detected by using the picture element pattern shown in FIG. 10A. FIGS. 11C and 11D show two patterns similar to but inclined at 45° with those shown in FIGS. 11A and 11B. In this case, as is apparent from FIG. 11C, it is impossible to detect the defect by using the picture element pattern shown in FIG. 9A. However, as is known from FIG. 11D, the defect can be detected by using the picture element pattern shown in FIG. 10H. As mentioned above, by using an axially asymmetric picture element pattern, a fine defect can be detected, and thus the defect detection sensitivity is enhanced. Accordingly, in the case where a pattern arranged in the X- and Y-directions and a 45° pattern are included in a pattern to be inspected, a pattern defect can be detected with high accuracy, by using both an axially symmetric picture element pattern and an axially asymmetric picture element pattern. In the above-mentioned explanation, a positioning error which does not exceed ±3 bits (or picture elements) has been detected. In order to detect a larger positioning error, it is necessary to increase the number of shift registers such as the shift registers $27_1$ to $27_6$, the number of shift registers such as the shift registers $28_1$ to $28_3$, the number of shift registers such as the shift registers $29_1$ to $29_7$, the number of exclusive OR gates such as the gates $31_1$ to $31_{49}$, the number of counters such as the counters $32_1$ to $32_{49}$, the number of bits included in each of shift registers such as the shift registers $29_1$ to $29_7$, and the number of bits included in the shift register 30. Further, in the above-mentioned explanation, two patterns formed on the same sample are detected and compared, to detect a pattern defect. However, a pattern on a sample and a corresponding pattern on a different sample may be detected and compared. Further, a binary signal corresponding to a reference pattern on a sample may be taken out of design data which is previously stored in storage means, to be compared with a binary signal corresponding to a to-be-inspected pattern.

In order to be able to detect a pattern defect even when the thermal drift in optical and mechanical systems cannot be neglected and the positioning accuracy of a sample holding stage is not good, a pattern defect detecting apparatus is required to be large in size. Accordingly, it is desired that the position of one of imaging devices is adjustable in each of the X- and Y-directions, as is shown in U.S. application Ser. No. 397,900, now U.S. Pat. No. 4,508,453, issued Apr. 12, 1985, and EPC Application No. 82106185.0. In such a case, the positioning error is measured in a scanning area, and a measured value which occurs most frequently when the whole of a pattern is scanned, is judged to be a true positioning error. An XY-table carrying the imaging device is moved in the X- and Y-directions by the true positioning error, and then the scanning operation is resumed. The above processing is repeated. Thus, a pattern defect can be detected with high accuracy, without making the structure of the pattern defect detecting apparatus more complicated.

As has been explained in the foregoing, according to the present invention, each time two binary signals corresponding to two patterns are delayed by a predetermined amount, the positioning error between the patterns is detected in the delay period by the novel method, and one of the delayed binary signals is corrected on the basis of the detected positioning error, to be compared with the other delayed binary signal. Further, even when a 45° pattern is included in each of two patterns to be compared with each other, the 45° pattern is detected with high accuracy, and therefore a pattern defect can be detected with high accuracy.

Figure 12:
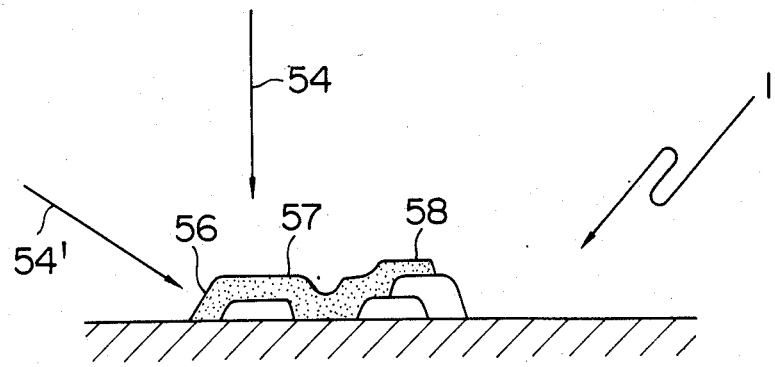
FIG. 12 is an enlarged cross-sectional view showing an example of an aluminum wiring pattern formed on a wafer.

Next, a method of detecting the pattern defect on an aluminum wiring pattern of a wafer will be explained, with reference to FIGS. 12 to 16B. This method is applicable to the pattern defect detecting apparatus shown in FIG. 5. In order to detect various defects in an aluminum wiring pattern formed on a wafer such as the short-circuit, line breakage, and unevenness of surface, it is necessary to discriminate the aluminum wiring pattern from other patterns on the wafer. FIG. 12 shows, in cross section, a portion of a pattern formed on a wafer which is to be observed. In FIG. 12, reference numeral 1 designates a wafer, 58 an aluminum wiring pattern to be detected, 56 a step portion of the wiring pattern 58, and 57 a planar portion of the wiring pattern. When the aluminum wiring pattern having such a cross section is illuminated with vertical illumination light as indicated by an arrow 54, the planar portion 57 is well lighted, and the step portion 56 is ill lighted. When dark field illumination light is incident on the aluminum wiring pattern as indicated by an arrow 54', the step portion 56 is well lighted, and the planar portion 57 is ill lighted.

FIGS. 13A to 13D are views for explaining detection signals which are obtained when the aluminum wiring pattern shown in FIG. 12 is scanned in a direction from left to right. FIG. 13C shows the same aluminum wiring pattern as in FIG. 12, to compare the wiring pattern with the detection signals. FIG. 13A is a graph showing a detection signal which is obtained when the wiring pattern is illuminated with vertical illumination light. FIG. 13B is a graph showing a detection signal which is obtained when the wiring pattern is illuminated with dark field illumination light. As can be seen from FIGS. 13A to 13C, when the wiring pattern is illuminated with the vertical illumination light and dark field illumination light, a detection signal such as shown in FIG. 13D is obtained.

FIGS. 14A and 14B are views for explaining, in more detail, the relation between the shape of wiring pattern and a detection signal. Referring to FIG. 14B, when vertical illumination light 54 and dark field illumination light 54' are incident on fine aluminum wiring patterns 58a each having a semicylindrical shape as well an aluminum wiring pattern 58 having a step portion 56 and a planar portion 57, each fine pattern 58a has a low reflectance for the vertical illumination light 54. While, a planar portion 61 which does not have any aluminum wiring pattern but is coated with, for example, an $SiO_2$ film, has a relatively high reflectance for the vertical illumination light 54. As a result, a detection signal such as shown in FIG. 14A is obtained. It is difficult to discriminate the aluminum wiring patterns from other patterns on the basis of such a detection signal. Accordingly, defects in the aluminum wiring patterns cannot be detected.

FIGS. 15A to 15D are views for explaining optical images of a wafer surface formed by reflected light.

FIG. 15A is a plan view showing part of the surface. In FIG. 15A, reference numeral 57 designates a planar portion of an aluminum pattern, 60 the top of a fine aluminum portion, and 61 a planar portion having no aluminum pattern. Incidentally, a region F bounded by a dot-dash line indicates a planar area of the planar portion 57. When dark field illumination given to the wafer surface is made for stronger than ordinary dark field illumination, a portion of the planar area F becomes bright for the following reason. That is, fine crystals which are called "hillock", are deposited on the surface of the aluminum wiring pattern, and dark field illumination light incident obliquely upon the aluminum pattern is subjected to diffused reflection at the hillock. Thus, a portion of reflected light is incident on an object lens. However, the quantity of light reflected from a central portion of the planar area F is small. Accordingly, when the reflected light incident on an imaging device is converted into a binary signal, an image such as shown in FIG. 15B is formed by the binary signal. That is, a dark spot 59 is formed at the center of the planar area F.

When strong vertical illumination is given to the pattern shown in FIG. 15A and the intensity of reflected light is converted into a binary signal, an image such as shown in FIG. 15C is formed by the binary signal. In FIG. 15C, reference symbol 61' designates the image of the planar portion 61 having no aluminum pattern, 57' the image of the planar portion 57 of the aluminum pattern, and 60' the image of the top 60 of the fine aluminum portion.

The images shown in FIGS. 15B and 15C are not suited to recognize the aluminum wiring pattern and detect a defect thereof. It is desirable to form such an image as shown in FIG. 15D. In this image, only the aluminum wiring pattern is clearly shown, and thus can be discrimated from other patterns. In order to clearly show only the aluminum wiring pattern as in FIG. 15D, the present inventors studied illumination conditions, that is, a wafer surface was illuminated with various quantities of vertical illumination light and various quantities of dark field illumination light, to find an optimum illumination condition.

FIG. 16A is a graph showing areas which can satisfactorily detect the planar portion and fine portion of the aluminum wiring pattern and were found by changing the intensity of vertical illumination light while keeping constant the intensity of dark field illumination light. In FIG. 16A, the intensity of vertical illumination light is plotted as abscissa, and the light detection level of the image sensors 18 and 19 as ordinate. In an area A shown in FIG. 16A, the planar portion of the aluminum wiring pattern can be satisfactorily detected. Further, in an area B, the fine portion of the aluminum wiring pattern can be satisfactorily detected. Accordingly, in the overlapping portion C of the areas A and B, both the planar portion and the fine portion of the aluminum wiring pattern can be satisfactorily detected.

FIG. 16B shows relations between the intensity of vertical illumination light and the video signal corresponding to the aluminum wiring pattern. A characteristic curve D shown in FIG. 16B indicates the signal level which was obtained at a bright region of the fine aluminum portion when the aluminum wiring pattern was illuminated with dark field illumination light, and a characteristic curve E indicates the signal level which was obtained at a bright region of the fine aluminum portion when the aluminum wiring pattern was illuminated with vertical illumination light. It was found that, when the signal level D at the bright region illuminated with dark field illumination light was higher than the signal level E at the bright region illuminated with vertical illumination light, excellent images of the planar and fine portions of the aluminum wiring pattern were formed as indicated by the overlapping portion C in FIG. 16A.

Next, explanation will be made on an illumination device according to the present invention which can illuminate a wafer in a desirable manner on the basis of the above-mentioned experimental fact, with reference to FIGS. 17 to 19. FIG. 19 shows an embodiment of an illumination device according to the present invention. In FIG. 17, reference numeral 1 designates a wafer, and 5 (or 6) an object lens. Referring to FIG. 17, a lamp 62 for dark field illumination is disposed on the optical axis of the object lens 5 (or 6), and a lamp 63 for vertical illumination is disposed separately from the lamp 62. A semitransparent mirror 53 is disposed so that a light beam 54 from the lamp 63 is reflected from the mirror 53 and the reflected light is directed to a reflecting mirror 70. A condenser lens 64, a field lens 65, and an aperture stop 66 for adjusting the light quantity of the light beam 54 are disposed between the lamp 63 and the mirror 53.

While, a parabolic mirror 69 is disposed so as to reflect light from the lamp 62 in directions 54' parallel to the optical axis of the object lens 5 (or 6), and another parabolic mirror 68 is disposed in the vicinity of an end portion of the object lens 5 (or 6) so that light travelling in the directions 54' is reflected from the parabolic mirror 68 and the reflected light impinges obliquely on the surface of the wafer 1. The light reflected from the wafer surface is detected by a linear image sensor 18 (or 19) which is formed of a charge coupled device or the like.

FIG. 18 is a schematic view showing the dark field illumination system extracted from the illumination device shown in FIG. 17. FIG. 19 is a schematic view showing an example of a conventional illumination device. In the conventional illumination device shown in FIG. 19, a single lamp 74 is used both for vertical illumination and for dark field illumination, and a reflecting mirror 72 is disposed around a semitransparent mirror 71. Further, a parabolic mirror 68 is disposed in the vicinity of an end portion of an object lens 5. While, in the optical system shown in FIG. 18, the lamp 62 only for dark field illumination is disposed so that light from the lamp 62 is reflected by the parabolic mirrors 69 and 68 and then impinges obliquely on the surface of the wafer 1. The optical system shown in FIG. 18 is suitable for giving strong, dark field illumination to the surface of the wafer 1.

Next, explanation will be made on a method of illuminating a wafer satisfactorily by using the illumination device shown in FIG. 17. As has been explained with reference to FIG. 18, the device shown in FIG. 17 can produce strong, dark field illumination. Accordingly, the surface of the wafer is illuminated with dark field illumination light to such an extent as to be able to detect the reflected light from a planar portion of a specified wiring pattern (for example, an aluminum wiring pattern). In other words, the surface of the wafer is put in such a state as shown in FIG. 15B. That is, the spot 59 at the center of the planar area F is ill lighted, but the peripheral portion 59' of the planar area F is well lighted. In addition to the above-mentioned dark field illumination light, the light beam 54 from the lamp 63 (for vertical illumination) is incident on the surface of the wafer 1 through the semitransparent mirror 53, reflecting mirror 70, and object lens 5 (or 6). The quantity of the vertical illumination light is adjusted by the aperture stop 66 so as to be minimum in a range capable of making the dark spot 59 bright. Thus, the dark spot is removed from the image shown in FIG. 15B. Moreover, since the quantity of vertical illumination light is made minimum in the above-mentioned range, there is no fear of the image 61' of the planar portion having no aluminum pattern, appearing as shown in FIG. 15C. In other words, in order to prevent the bright image 61' of the planar portion having no aluminum pattern from appearing as shown in FIG. 15C, the signal level due to vertical illumination is made lower than the signal level due to dark field illumination. Thus, the dark spot 59 is removed from the image shown in FIG. 15B, and an image such as shown in FIG. 15D, that is, an image which clearly shows only the aluminum pattern, is obtained.

FIG. 20 shows an optical system which is incorporated in the pattern defect detecting apparatus shown in FIG. 5. Referring to FIG. 20, a wafer 1 is placed on a Z-table (not shown) which can be inclined at a desired angle to a horizontal plane and can move in the Z-direction (namely, vertical direction) as disclosed in a Japanese Patent Application Specification (Laid-open No. 73117/1983). The Z-table is mounted on the X-Y-$\theta$ stage 2 shown in FIG. 1. A pair of optical units, each of which includes the lamp for dark field illumination, two parabolic mirrors, reflecting mirror, and object lens as shown in FIG. 17, are spaced apart from each other in accordance with the distance between two chips to be imaged. The two optical units use a lamp 63 for vertical illumination in common. Filters 76A and 76B are used for cutting off infrared rays. That is, red light and light shorter in wavelength than red light are used as vertical illumination light. Reference symbols 75A, 75B, 77A, 77B, 78A, and 78B designate reflecting mirrors, 79A, 79B, 80A, 80B, 81A, and 81B lenses, 82A and 82B field lenses, and 83A and 83B magnification changing lenses. Filters 84A and 84B cut off infrared rays and red light. Thus, light shorter in wavelength than red light is used as dark field illumination light. Further, reference symbols 85A and 85B designate filters for transmitting only red light, and 86A and 86B mirrors. In order to ascertain that the surface of the wafer 1 is focussed on the linear image sensors 18 and 19, linear stripe patterns 87A, 87B, 88A, and 88B are disposed before and after each of focal points F.P., and are projected on the wafer 1. The contrast of the stripe pattern thus projected is detected by two-dimensional array sensors 89A and 89B each having the form of a matrix. As disclosed in a Japanese Patent Application Specification (Laid-open No. 70540/1983), the two-dimensional array sensors 89A and 89B detect the contrast of the stripe pattern, and the Z-table is moved in the Z-direction or inclined so that two stripe patterns become equal sensitivity to each other. Thus, the surface of the wafer 1 is focussed on the linear image sensors 18 and 19. Further, reference symbols 90A and 90B designate semitransparent mirrors, 91A, 91B, 92A, 92B, 93A, and 93B lenses, 94A and 94B semitransparent mirrors, 95A and 95B television cameras for imaging the surface of the wafer, 96 a monitor for monitoring the wafer surface, 97A and 97B mirrors, 98A and 98B lenses, and 99A and 99B eyepieces. That is, the surface of the wafer 1 is monitored, and moreover can be visually observed.

A surface area of the wafer 1 on which the linear stripe pattern is projected, is different from a surface area imaged by the image sensor 18 or 19. Further, the linear stripe pattern is projected on such a plane as shown in FIG. 15A so that the image of the stripe pattern makes an angle of 45° with the IC chip circuit patterns on the wafer. Accordingly, the two-dimensional image sensors 89A and 89B can detect the image of the stripe pattern without being affected by the patterns on the wafer. Details of the detection of stripe pattern is described in the previously-referred Japanese Patent Application Specification (Laid-open No. 70540/1983).

As has been explained in the above, when an illumination device according to the present invention is employed, a wiring pattern (made of aluminum or others) can be readily discriminated from other patterns formed on a wafer.

We claim:

1. A method of detecting a pattern defect in accordance with the difference between a pair of patterns comprising the steps of:
    (a) obtaining a first binary signal by scanning and imaging one of said patterns;
    (b) obtaining a second binary signal corresponding to the other pattern by scanning and imaging the other of said patterns or from information previously stored in storage means;
    (c) detecting, two-dimensionally, a positioning error between said patterns, during a period when said first and second binary signals are delayed by a predetermined amount, in such a manner that each of the picture elements included in a predetermined area of a two-dimensional image, which is delayed and cut out two-dimensionally corresponding to said one pattern, is compared with a specified picture element included in a predetermined area of an image which is delayed and cut out two-dimensionally corresponding to said other pattern, such that the result of said comparison is summed statistically and each of said picture elements in accordance with said scanning, and such that said positioning error is detected by detecting a position shown as an extreme value two-dimensionally from said summed values;
    (d) correcting said positioning error by two-dimensionally shifting at least one of said first and second binary signals which have been delayed by said predetermined amount according to said detected positioning error; and
    (e) two-dimensionally comparing the first and second binary signals which have been corrected and extracted with each other.

2. A method of detecting a pattern defect according to claim 1, wherein said binary signals are simultaneously extracted from said first and second binary signals which have been corrected, in accordance with a picture element pattern which has only one axis of symmetry.

3. A method of detecting a pattern defect according to claim 8, wherein each of said patterns is a wiring pattern formed on a wafer.

4. A method of detecting a pattern defect according to claim 3, wherein said wafer is illuminated with both vertical illumination light and illumination light incident at an acute angle thereon.

5. An apparatus for detecting a pattern defect in accordance with the difference between a pair of patterns comprising:
- means for obtaining a first binary signal by scanning and imaging one of said patterns;
- means for obtaining a second binary signal corresponding to the other pattern by scanning and imaging the other of said patterns or from information previously stored in storage means;
- means for two-dimensionally detecting the positioning error between said patterns during a period when said first and second binary signals are delayed by a predetermined amount, by comparing each of picture elements included in a predetermined area of a two-dimensional image, which is delayed and cut out two-dimensionally corresponding to said one pattern with a specified picture element included in a predetermined area of an image which is delayed and cut out two-dimensionally corresponding to the other of said patterns, and summing statistically the comparison result for each of said picture elements in accordance with said scanning and producing a positioning error by detecting a position shown as an extreme value two-dimensionally from said summed values;
- means for correcting said positioning error by two-dimensionally shifting at least one of said first and second binary signals which have been delayed by said predetermined amount according to said detected positioning error; and
- means for two-dimensionally comparing the first and second binary signals which have been corrected and extracted with each other.

6. An apparatus according to claim 5, wherein said binary signals are simultaneously extracted from said first and second binary signals which have been corrected, in accordance with a picture element pattern which has only one access of symmetry.

7. An apparatus according to claim 5, further comprising illumination means in which a lamp for vertical illumination and a lamp for inclined illumination incident at an acute angle thereon are severally provided, means for adjusting the quantity of vertical illumination light from said lamp for vertical illumination is provided to adjust a ratio of the quantity of vertical illumination light to the quantity of illumination light, a first parabolic mirror is disposed so as to reflect light from the lamp for inclined illumination in directions parallel to the optical axis of an object lens, and a second parabolic mirror is disposed in the vicinity of an end portion of said object lens so that light travelling in the directions parallel to the optical axis of the object lens is reflected from said second parabolic mirror and the reflected light from the second parabolic mirror impinges obliquely on a portion to be illuminated, said illumnation means being disposed so that the image of said one pattern illuminated with said illumination means is formed on said imaging means by reflected light from said pattern.

* * * * *